United States Patent [19]

Chance et al.

[11] 4,006,274
[45] Feb. 1, 1977

[54] 2,4,6-TRIS(CARBAMOYLMETHYLAMINO)-1,3,5,-S-TRIAZINE

[75] Inventors: Leon H. Chance, New Orleans; Judy D. Timpa; George L. Drake, Jr., both of Metairie, all of La.

[73] Assignee: The United States of America as represented by the Secretary of Agriculture, Washington, D.C.

[22] Filed: Sept. 19, 1975

[21] Appl. No.: 615,015

[52] U.S. Cl. .......................... 427/381; 260/249.6; 427/382; 427/390 C; 427/392; 427/394; 427/396
[51] Int. Cl.² ............................................ B05D 3/02
[58] Field of Search .............. 260/249.6; 427/394, 427/390 C, 392, 396, 381, 382

[56] References Cited

UNITED STATES PATENTS

| | | | |
|---|---|---|---|
| 3,374,235 | 3/1968 | Varsanyi et al. | 260/249.6 |
| 3,519,625 | 7/1970 | Beacham et al. | 260/249.6 |
| 3,526,622 | 9/1970 | Varsanyi et al. | 260/249.6 X |
| 3,562,158 | 2/1971 | Varsanyi et al. | 260/249.6 X |
| 3,634,422 | 1/1972 | Nachbur et al. | 260/249.6 |

*Primary Examiner*—Michael R. Lusignan
*Attorney, Agent, or Firm*—M. Howard Silverstein; David G. McConnell; Salvador J. Cangemi

[57] ABSTRACT

2,4,6-Tris(carbamoylmethylamino)-1,3,5-s-triazine, abbreviated TCMT, is prepared by the reaction of 2,4,6-tris(carbethoxymethylamino)-1,3,5-s-triazine with ammonia. The methylol derivative of TCMT is prepared and applied to cotton textiles and blends of cotton and polyester to impart wrinkle recovery thereto.

1 Claim, No Drawings

2,4,6-TRIS(CARBAMOYLMETHYLAMINO)-1,3,5,-S-TRIAZINE

This invention relates to a new organic compound and to a process for the preparation of the compound. More specifically the invention relates to 2,4,6-tris(carbamoylmethylamino)-1,3,5 -s-triazine, hereinafter referred to as TCMT, and to its methylol derivatives. The methylol derivatives are useful in the preparation of resins, and in their application to cellulosic textiles to impart wrinkle recovery thereto. The resins are particularly useful in imparting wrinkle recovery to cotton textiles or cotton and polyester blends.

According to the present invention, TCMT is prepared by the reaction of 2,4,6-tris(carbethoxymethylamino)-1,3,5-s-triazine with ammonia. This is represented by the following equation;

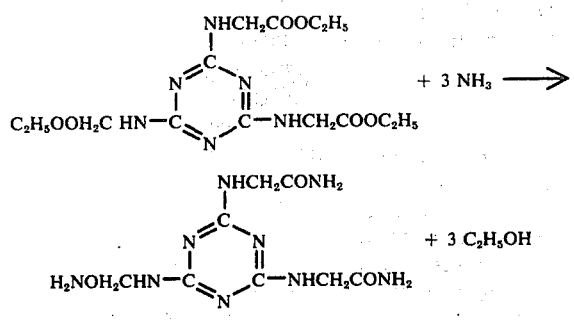

The triazine ester in the above equation may be conveniently prepared by the method of Hans Nestler and Hans Fürst by the reaction of cyanuric chloride with glycine ethyl ester hydrochloride in the presence of potassium carbonate (Reference J. Prakt. Chem. 22(3–4), 173–85 [1963]). The reaction of the ester may be carried out at about from 20° C to about 30° C for periods of time ranging about from 26 hours to about 66 hours. It is preferable to carry out the reaction in excess aqueous ammonia because when alcoholic ammonia is used a mixture of products is obtained. It is also preferable to carry out the reaction at 27° C to 29° C for about 26 hours.

In the preparation of the methylol derivatives of TCMT, the reaction of TCMT with formaldehyde is carried out in alkaline aqueous solution by boiling until the TCMT dissolves. This requires about from 2 minutes to about 5 minutes, depending on the mole ratio of TCMT to formaldehyde, the rate of heating, and the quantity of solution. The mole ratio of TCMT to formaldehyde may be varied about from 1:3.5 to 1:9. The preferred ratio is 1:3.5. At this mole ratio the solution consists primarily of the trimethylol derivative of TCMT. In the application of the trimethylol derivative to textiles a latent acid catalyst is required. The catalyst may be any suitable catalyst such as $Zn(NO_3)_2 \cdot 6H_2O$ $MgCl_2 \cdot 6H_2O$ or a mixed catalyst containing a 1:1 mole ratio of citric acid and $MgCl_2 \cdot 6H_2O$. The textile is impregnated with the solution and dried at about from 60° C to 85° C for about 3 minutes to 7 minutes, and cured at 150° C about from 3 minutes to 5 minutes. The treated textiles have improved wrinkle recovery properties as measured by the AATCC Test Method 66-1968.

One advantage of the methylol derivatives of TCMT is that the solutions are quite stable for use in treating textiles. Another advantage is that the reaction on cotton fabrics is very efficient. Still another advantage is that textiles treated with methylol derivative have a soft hand.

The following examples illustrate procedures that have been used successfully in carrying out the invention and are not meant as a limitation thereof.

EXAMPLE 1

Preparation of TCMT 90 grams (0.23 mole) of 2,4,6-tris(carbethoxymethylamino)-1,3,5-s-triazine and 1 liter of concentrated ammonium hydroxide (containing 28–30% ammonia) were stirred in a stoppered flask for about 66 hours at room temperature (27°–29° C). White crystals of TCMT separated. The flask was cooled in a refrigerator to obtain maximum crystallization. The crystals were filtered and washed with cold water. The dried crystales weighed 56.7 grams — a yield of 81.5% of TCMT. The melting point was 278°–279° (with decomposition). A yield of 81.9% was obtained by carrying out the reaction in the same manner for only 26 hours. An analytical sample of TCMT was prepared by dissolving 2 grams of TCMT in 75 ml of boiling water and cooling to allow crystallization. Analysis: Calculated for $C_9H_{15}N_9O_3$: C, 36.36; H, 5.09; N, 42.40. Found: C, 36.49; H, 5.05; N, 42.21.

EXAMPLE 2

Preparation of Methylol Derivatives of TCMT and their application to textiles 6.0 grams (0.02 mole) of TCMT was placed in a beaker with 40 ml of water and 5.68 grams (0.07 mole) of 37% aqueous formaldehyde. This represented a mole ratio of TCMT: HCHO of 1:3.5. The mixture was adjusted to pH 8.9 by adding 3 drops of 5% sodium hydroxide. The mixture was placed on a pre-heated hot plate and heated with stirring. After 3 minutes, 5 more drops of 5% sodium hydroxide was added. All of the TCMT dissolved when the mixture began to boil. This required a total heating time of about 4½ minutes. The solution was immediately cooled by placing the beaker in ice water. The pH was acidic at this point. It was readjusted to a pH of 9.3 by adding 5% NaOH. The solution was divided into three equal parts. Each part weighed 17.2 grams and was labeled solutions 1, 2, and 3. Solution No. 1 was left as is, while sufficient 37% was added to solutions 2 and 3 to give TCMT:HCHO ratios of 1:6 and 1:9, respectively. The three solutions were finally adjusted to pH 9.5 and allowed to stand overnight for about 18 hours at room temperature (about 26° C). The pH of each solution at this point was about 7.2. Each solution was adjusted to pH 6.7–6.8 by addition of 1% hydrochloric acid. To each solution was added sufficient catalyst to give a solution containing 0.5% solid catalyst based on the total weight of the solution. The catalyst was a 20% solution of a mixed catalyst containing a 1:1 mole ratio of citic acid and $MgCl_2 \cdot 6H_2O$. Each solution was finally diluted to 10% reactive solids based on the trimethylol derivative of TCMT. Solutions 2 and 3 probably contained a mixture of methylol derivatives with 3 moles or more of combined formaldehyde. The final pH of solutions 1, 2, and 3 was 4.30, 4.05, and 3.95, respectively.

Each solution was padded on to samples of cotton printcloth, using laboratory padder, to a wet pickup of about 90%. The samples were then dried for 3 minutes at 85° C and cured for 5 minutes at 150° C, rinsed and dried. The fabric sample treated with solution 1 had a weight gain of 8.4% and a wrinkle recovery angle of 252° (warp plus fill). The fabric treated with solutions 2 and 3 had weight gains of 8.5% and 10.1%, respectively. The wrinkle recovery angles were 271° and 287°, respectively. None of the samples were discolored by the treatment and all of the samples had a good soft hand. The efficiencies of the reactions on these fabric samples based on the trimethylol derivative were 95%, 97%, and 111%, respectively.

The same solutions were allowed to age for 27 hours at room temperature (27° C), and applied to cotton print-cloth as before. The fabric weight gains from solutions 1, 2, and 3 were 7.7%, 7.6% and 9.1%, respectively. The wrinkle recovery angles were 251°, 256°, and 276° (warp plus fill), respectively. The untreated fabric had a wrinkle recovery of 179° (warp + ). The fabrics were not discolored and still had a good soft hand. The same solutions still had not deposited polymers even after standing for 3 days. This indicated that the solutions were quite stable.

EXAMPLE 3

20.2 grams (0.067 mole) of TCMT was placed in a 500 ml flask equipped with a stirrer, reflux condenser, and dropping funnel. Water (150 grams) was added and the mixture heated to 90°–95° C. Then 19.0 grams of 37% formaldehyde (0.234 mole), to which several drops of 20% sodium hydroxide had been added, was added all at once through the dropping funnel. The flask was stirred and heating was continued. The TCMT dissolved within about 2 to 4 minutes. The flask was immediately cooled to room temperature by placing in ice water. The pH was adjusted to 9.0 with 20% NaOH. It was allowed to stand overnight. The pH was about 7.0 at this point. The solution was divided into two equal portions. The one was added $Zn(NO_3)_2·6H_2O$ such that the concentration of catalyst was 1% based on the total weight of the final solution. The solution was diluted with enough water to make a total of 10% reactive solids based on the trimethylol derivative of TCMT. The solution also contained 0.1% wetting agent and 0.5% of a polyethylene softener. The other solution was identical except that it contained 1% of a mixed catalyst (1:1 mole ratio of citric acid and $MgCl_2·6H_2O$).

Samples of cotton printcloth and of a 50/50 blend of cotton/polyester printcloth were treated with the above solution. The fabrics were treated as in Example 2 except that they were dried for 7 minutes at 60° C and cured for 3 minutes at 150° C. The wrinkle recovery data are shown in Table I.

TABLE I

| Type Fabric | Catalyst | Wrinkle recovery warp + Fill (°) |
|---|---|---|
| Cotton | mixed | 269 |
| cotton | $Zn(NO_3)_2$ | 266 |
| 50/50 blend | mixed | 277 |
| 50/50 blend | $Zn(NO_3)_2$ | 283 |
| cotton control | — | 179 |
| blend control | — | 254 |

The wrinkle recovery of all of the treated fabrics was greater than the control fabrics. All of the fabrics had a good soft hand, no discoloration, and had good strength and abrasion resistance properties.

EXAMPLE 4

Preparation of Resins

A water solution of the trimethylol derivative prepared as in Example 3, was acidified by adding a solution of zinc nitrate. The solution was heated for 30 minutes at 90° C on a watch glass. A clear hard colorless resin was formed. When the resin was further cured for 5 minutes at 155° C it became slightly yellow in color.

We claim:
1. A process for imparting to cotton and cotton-polyester blended fabric a soft hand in combination with wash-wear properties, the process comprising:
   a. impregnating a cellulosic fabric with an aqueous solution containing about 10% of trimethylol derivative of 2,4,6-Tris (cabamolymethylamino)-1,3,5-s-triazine and about from 0.5% to 1.0% of a catalyst selected from the group consisting of:
   $Zn(NO_3)_2·6H_2O$,
   $MgCl_2·6H_2O$, and a
   1:1 mole ratio of citric acid and $MgCl_2·6H_2O$,
   b. dying the wet impregnated fabric at about 60° to 85° C for 3–7 minutes, and
   c. curing at about 150° for 3–5 minutes.

* * * * *